United States Patent
Goodbrand et al.

(10) Patent No.: US 7,138,555 B2
(45) Date of Patent: Nov. 21, 2006

(54) PROCESS FOR PREPARING IODOAROMATIC COMPOUNDS AND USING THE SAME

(75) Inventors: H. Bruce Goodbrand, Hamilton (CA); Timothy P. Bender, Port Credit (CA); Roger E. Gaynor, Oakville (CA); Leanne Murphy, Mississauga (CA)

(73) Assignee: Xerox Corporation, Stamford, CT (US)

( * ) Notice: Subject to any disclaimer, the term of this patent is extended or adjusted under 35 U.S.C. 154(b) by 373 days.

(21) Appl. No.: 10/709,193

(22) Filed: Apr. 20, 2004

(65) Prior Publication Data

US 2005/0234272 A1     Oct. 20, 2005

(51) Int. Cl.
C07C 17/20 (2006.01)
(52) U.S. Cl. .................................... 570/206; 570/190
(58) Field of Classification Search ................ 570/206, 570/190

See application file for complete search history.

(56) References Cited

U.S. PATENT DOCUMENTS

| | | | |
|---|---|---|---|
| 3,180,730 A | 4/1965 | Klupfel et al. | |
| 4,265,990 A | 5/1981 | Stolka et al. | |
| 4,764,625 A | 8/1988 | Turner et al. | |
| 5,220,020 A | 6/1993 | Buchwald et al. | |
| 5,227,538 A | 7/1993 | Buchwald et al. | |
| 5,286,878 A | 2/1994 | Buchwald et al. | |
| 5,292,893 A | 3/1994 | Buchwald et al. | |
| 5,442,119 A | 8/1995 | Buchwald et al. | |
| 5,489,682 A | 2/1996 | Buchwald et al. | |
| 5,491,233 A | 2/1996 | Buchwald et al. | |
| 5,576,460 A | 11/1996 | Buchwald et al. | |
| 5,847,166 A | 12/1998 | Buchwald et al. | |
| 5,856,596 A | 1/1999 | Nukada | |
| 6,072,085 A | 6/2000 | Verdaugur et al. | |
| 6,166,226 A | 12/2000 | Buchwald et al. | |
| 6,235,871 B1 | 5/2001 | Singer et al. | |
| 6,235,936 B1 | 5/2001 | Buchwald et al. | |
| 6,307,087 B1 | 10/2001 | Buchwald et al. | |
| 6,323,366 B1 | 11/2001 | Wolfe et al. | |
| 6,395,916 B1 | 5/2002 | Buchwald et al. | |
| 6,465,693 B1 | 10/2002 | Buchwald et al. | |
| 2002/0156295 A1 | 10/2002 | Buchwald et al. | |
| 2004/0010149 A1 | 1/2004 | Buchwald et al. | |

FOREIGN PATENT DOCUMENTS

| JP | B 55-042380 | 3/1980 |
|---|---|---|
| JP | B 56-040835 | 4/1981 |
| JP | A 58-0198043 | 11/1983 |
| JP | A 63-314554 | 12/1988 |
| JP | A 01-280763 | 11/1989 |
| JP | A 02-178666 | 7/1990 |
| JP | A 02-178667 | 7/1990 |
| JP | A 02-178668 | 7/1990 |
| JP | A 02-178669 | 7/1990 |
| JP | A 02-178670 | 7/1990 |
| JP | A 02-190862 | 7/1990 |
| JP | A 02-190863 | 7/1990 |
| JP | A 02-230255 | 9/1990 |
| JP | A 03-078755 | 4/1991 |
| JP | A 03-078756 | 4/1991 |
| JP | A 03-078757 | 4/1991 |
| JP | A 03-144058 | 6/1991 |
| JP | A 04-133064 | 5/1992 |
| JP | A 04-193852 | 7/1992 |
| JP | A 04-0312558 | 11/1992 |
| JP | A 05-019509 | 1/1993 |
| JP | A 05-080550 | 4/1993 |
| JP | A 05-313386 | 11/1993 |

OTHER PUBLICATIONS

Artis Klapars and Stephen L. Buchwald, *Copper-Catalyzed Domino Halogen Exchange-Cyanation of Aryl Bromides*, J. Am Chem. Soc. 2003, 125, 2890-2891 (web release Feb. 15, 2003).

Artis Klapars and Stephen L. Buchwald, *Copper-Catalyzed Halogen Exchange in Aryl Halides: An Aromatic Finkelstein Reaction*, J. Am Chem. Soc. 2002, 124, 14844-14845 (web release Nov. 20, 2002).

Cristau H. et al., *Mild and Efficient Copper-Catalyzed Cyanation of Aryl Iodides and Bromides*; Chemistry A European Journal; vol. 11, 2483-2492; 2005.

*Primary Examiner*—Elvis O. Price
(74) *Attorney, Agent, or Firm*—Oliff & Berridge, PLC

(57) ABSTRACT

The present invention provides a process for preparing monoiodinated aromatic compounds that are useful as intermediates for preparing charge transporting and hole transporting amino compounds and have high purity with high yield and at low cost. A process for preparing aryl iodide compounds comprises reacting an aryl halide compound with a metal iodide, a metal catalyst and a catalyst coordinating ligand in at least one solvent to form an aryl iodide; and purifying the aryl iodide. A triarylamine compound and a process for preparing a triarylamine compounds reacting the aryl iodide with a diarylamine is also provided. Further, a photoconductive imaging member comprising a charge transport layer that comprises at least one triarylamine compound prepared reacting the aryl iodide with a diarylamine is provided.

17 Claims, No Drawings

PROCESS FOR PREPARING IODOAROMATIC COMPOUNDS AND USING THE SAME

BACKGROUND OF THE INVENTION

1. Field of the Invention

This invention relates to processes for preparing iodoaromatic compounds. This invention further relates to the use of iodoaromatic compounds in the formation of triarylamine hole transport small molecules, which may be used in electrophotography.

2. Description of Related Art

Electrophotographic imaging members (i.e. photoreceptors) are well known. Electrophotographic imaging members are commonly used in electrophotographic (xerographic) processes and may comprise a photoconductive layer including a single layer or composite layers. These electrophotographic imaging members take many different forms. For example, layered photoresponsive imaging members, such as those described in U.S. Pat. No. 4,265,990 to Stolka et al., which is incorporated by reference in its entirety, are known in the art.

More advanced photoconductive photoreceptors containing highly specialized component layers are also known. For example, a multilayered photoreceptor employed in electrophotographic imaging systems sometimes includes one or more of a substrate, an undercoating layer, an intermediate layer, an optional hole or charge blocking layer, a charge generating layer over an undercoating layer and/or a blocking layer, and a charge transport layer (including a charge transport material in a binder). Additional layers such as one or more overcoating layer or layers are also sometimes included.

Various compounds are known for their uses as charge transporting materials, including hole transporting materials, in charge transporting layers of electrophotographic apparatuses, including pyrazoline compounds such as those disclosed in JP-B-37-10696, triarylamine compounds such as those disclosed in U.S. Pat. No. 3,180,730 to Klupfel et al., stilbene compounds as disclosed in published unexamined Japanese Patent Application JP-A-58-198043, hydrazone compounds as disclosed in JP-B-55-42380, oxadiazone compounds as disclosed in JP-B-34-5466, butadiene compounds as disclosed in published unexamined Japanese Patent Application JP-A-63-314554, and so on, are known. Among these compounds, triarylamine compounds are of particular importance, in view of high charge-transporting and hole-transporting ability (mobility), and various triarylamine compounds have been disclosed, e.g., in JP-A-1-280763, JP-A-2-178666, JP-A-2-178667, JP-A-2-178668, JP-A-2-178669, JP-A-2-178670, JP-A-2-190862, JP-A-2-190863, JP-A-2-230255, JP-A-3-78755, JP-A-3-78756, JP-A-3-78757, JP-A-3-114058, JP-A-4-133064, JP-A-4-193852, JP-A-4-312558, JP-A-5-19509, JP-A-5-80550, and JP-A-5-313386.

It is generally known that triarylamine compounds can be synthesized by coupling an arylamine compound with an aryl halide, usually an aryl bromide or an aryl iodide, using a copper catalyst. Aryl iodides are preferred due to the low reactivity of aryl bromides during tertiary amine formation.

Typically, large-scale production of triarylamine small molecules is accomplished by use of an Ullmann condensation reaction, such as those illustrated in reaction schemes (1) and (2):

[Insert Chemical Drawing (1)]

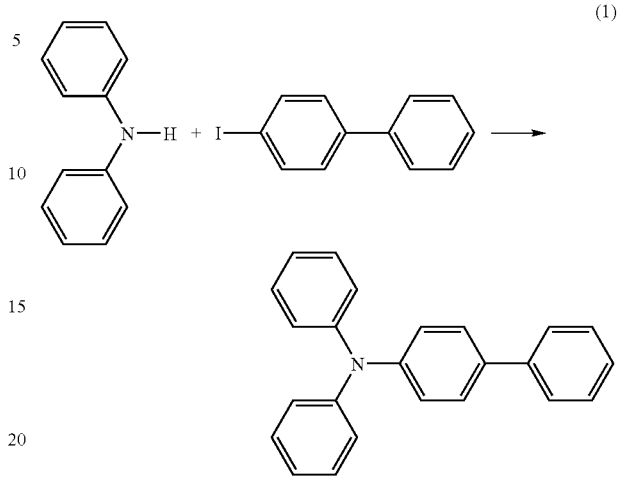

(1)

[Insert Chemical Drawing (2)]

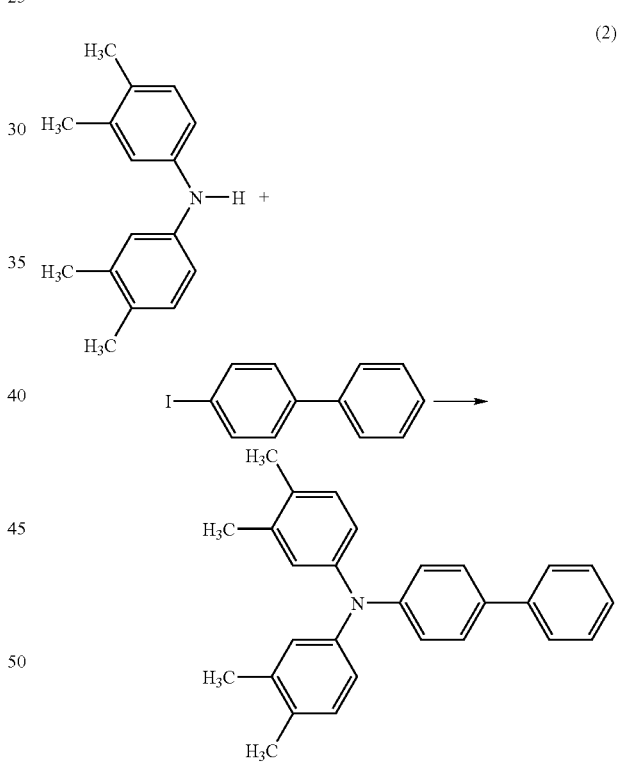

(2)

The use of Ullmann condensation reactions in the production of tertiary amines, specifically triarylamines, is described in detail in, for example, U.S. Pat. No. 4,764,625 to Turner, et al., the entire disclosure of which is incorporated herein by reference.

In such Ullmann condensation reactions, aromatic halides, such as aryl iodides, are reacted with aromatic amine compounds in the presence of a base, a copper catalyst and, optionally, an inert solvent. Aromatic iodides possess a much higher reactivity than other aromatic halides in these reactions. Typically, aryl iodides have higher kinetic rates of product formation than other aromatic halides, as illustrated by the reduced reaction times necessary to produce higher yields of highly pure products than with other aromatic halides. Thus, aryl iodides are key substrates in the Ullmann condensation reactions traditionally used to manufacture triarylamine hole transport small molecules.

However, the benefits of using aryl iodides to form triarylamines by Ullmann condensation are not without cost. Aryl iodides are generally more expensive than aryl bromides or aryl chlorides.

The formation of aryliodides by iodinating an aromatic compound with a sulfuric acid catalyst in a mixed water/acetic acid solvent, using iodic acid and iodine, as shown in Ann., 634, 84 (1960) is known, as exemplified by the iodination of biphenyl in reaction scheme (3). Reaction scheme (3) represents a common, currently employed manufacturing method for 4-iodobiphenyl.

[Insert Chemical Drawing (3)]

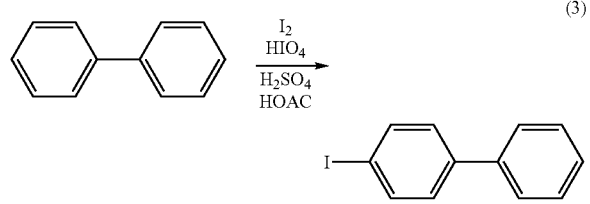

(3)

In this reaction, biphenyl is iodinated by a hypervalent iodine species, prepared from elemental iodine and periodic acid in a strongly acidic solution. Preparation of monoiodo compound by this method is difficult, at least because over-iodination occurs. In the reaction scheme (3) above, the reaction mixture contains starting material, 4-iodobiphenyl, and 1,4-diiodobiphenyl. In order to prepare the mono-iodo compound for use in an Ullmann condensation, extensive purification by recrystallization is necessary, and yields of only about 60% can be obtained.

Iodination with periodic acid is carried out with ease. However the reaction selectivity is low. The reaction product is a mixture of monoiodo and diiodo compounds. When a subsequent amination reaction is carried out using this mixture, the reaction product after amination also comprises a mixture. Since impurities in the amination product have detrimental effects on the electrical characteristics of the charge transport material, purification of the product is required. The molecular weight of the impurities is large enough to render purification by distillation, etc., impractical. Thus, a very expensive purification method, such as a column purification, etc., must be used. In addition to the expense of iodine, a method in which many diiodo byproducts are formed is a costly process for preparing arylamine compounds.

Also, the solubility of diiodo compounds is very low, the diiodo compound cannot be removed from the product by recrystallization, which may be easily incorporated into industrial operations at low cost. Therefore, for product mixtures containing about 10% or more of diiodo compounds, purification by distillation is required.

The monoiodo compound, in contrast, has a high boiling point and a high melting point. For these reasons, high vacuum conditions are required in the distillation of monoiodo compound, and the product recovered by distillation is apt to solidify and become difficult to handle. When the mixture to be subjected to distillation contains a large amount of diiodo compounds, distillation must be carried out multiple times. The purity of the product subjected to a single distillation is lowered by "splashing" of the distillation mixture, resulting in contamination of the distillation product by diiodo compounds. Thus, fractional distillation is required to purify the monoiodo product from a reaction mixture containing a large amount of diiodo compounds. The more involved purification process complicates operation and increases manufacturing costs.

Also, Ann., 634, 84 (1960) describes carrying out the iodination reaction in a saturated solution of an aromatic compound to increase the selectivity of monoiodo compound formation. This method, however, does not provide a low-cost product having sufficient purity as a raw material used for a charge transporting material.

The present invention is provided to solve the problems described above. That is, the present invention provides a low cost route to iodoaromatic molecules, having high yields of highly pure monoiodo compounds, and thus a low cost route to triarylamine hole transport small molecules.

SUMMARY OF THE INVENTION

The present invention provides a process for preparing mono-iodinated aromatic compounds having high purity with high yield and at low cost.

Further, the present invention provides a process for preparing mono-iodinated aromatic compounds that are useful as intermediates for preparing charge transporting and hole transporting amino compounds.

Specifically, this invention provides process for preparing an aryl iodide compound by reacting an aryl halide compound with a metal iodide, a metal catalyst and a catalyst coordinating ligand in at least one solvent to form an aryl iodide; and purifying the aryl iodide.

This invention separably provides an aryl iodide compound prepared by reacting an aryl halide compound with a metal iodide, a metal catalyst and a catalyst coordinating ligand in at least one solvent to form an aryl iodide; and purifying the aryl iodide.

This invention separably provides a process for preparing a triarylamine compound by reacting an aryl halide compound with a metal iodide, a metal catalyst and a catalyst coordinating ligand in at least one solvent to form an aryl iodide; purifying the aryl iodide, reacting the aryl iodide with a diarylamine in the presence of potassium hydroxide and a copper catalyst in at least one solvent to form a triarylamine, and purifying the triarylamine.

This invention separably provides a triarylamine compound prepared by reacting an aryl halide compound with a metal iodide, a metal catalyst and a catalyst coordinating ligand in at least one solvent to form an aryl iodide; purifying the aryl iodide, reacting the aryl iodide with a diarylamine in the presence of potassium hydroxide and a copper catalyst in at least one solvent to form a triarylamine, and purifying the triarylamine.

This invention further separably provides a photoconductive imaging member comprising a charge transport layer that comprises at least one triarylamine compound prepared by reacting an aryl halide compound with a metal iodide, a metal catalyst and a catalyst coordinating ligand in at least one solvent to form an aryl iodide; purifying the aryl iodide, reacting the aryl iodide with a diarylamine in the presence of potassium hydroxide and a copper catalyst in at least one solvent to form a triarylamine, and purifying the triarylamine.

DETAILED DESCRIPTION OF PREFERRED EMBODIMENTS

The iodination reaction is carried out by a catalyzed halogen exchange reaction in which an aryl halide compound, a metal iodide, a catalyst and a catalyst coordinating ligand are added to a solvent, and thereafter, the reaction mixture is heated. After the reaction mixture is cooled, the reaction product is isolated and may be used in preparation of triarylamine small molecules.

The aryl portion of the aryl halide compound is not particularly limited. The aryl portion may include, but is not limited to, benzyl, cyclopentadienyl, biphenyl, terphenyl, tolyl, naphthyl, anthryl, phenanthryl, pyryl, fluorenyl and the like. The aryl portion may include one or more substituent group. Such substituents are not particularly limited, and may include but are not limited to alkyl groups, alkoxy groups, amide groups, sulfonamide groups, indole groups, nitrile groups, ester groups, fluoride atoms and the like. The halide portion of the aryl halide may be a bromine or chlorine atom.

The metal iodide used in the iodination reaction is not particularly limited. In particular, Group I and Group II metal iodides may be used, and Group I iodides, such as lithium iodide, sodium iodide and potassium iodide, are preferred. The metal iodide may be present in any effective amount, but the metal iodide is generally present in excess, with respect to the aryl halide reactant. For example, the metal iodide may be present in an amount such that the ratio of iodine atoms to aryl halide reactant molecules is in the range of from about 1:1 to about 10:1, preferably in the range of from about 2:1 to about 5:1.

As the catalyst in the iodination reaction, any suitable transition metal catalyst may be used. In particular, copper catalysts may be used as the catalyst for the iodination reaction. Examples of copper catalysts include but are not limited to copper powder, cuprous oxide and copper I and copper II halides, such as copper I and copper II chlorides, bromides and iodides. In fact, any copper catalyst heretofore commonly used in the halogen exchange reactions can be employed.

The catalyst may be present in any effective amount. The catalyst is preferably present in an amount in the range of from about 1 mole % to about 50 mole % with respect to the amount of aryl halide, more preferably in the range of from about 2 mole % to about 10 mole % with respect to the amount of aryl halide, and even more preferably in an amount that is about 5 mole % with respect to the amount of aryl halide.

Any ligand suitable for use with the chosen catalyst may be used as the catalyst coordinating ligand in the iodination reaction. Diamine ligands are particularly useful as catalyst coordinating ligands for preparing aryl iodides by this iodination reaction. In particular, 1,2-diamine ligands and 1,3-diamine ligands are preferred, and 1,3-propanediamine is most preferred. In addition, mono- and bidentate nitrogen-containing heterocycle ligands, including but not limited to 1,10-phenanthroline, may be used as the catalyst coordinating ligand.

The catalyst coordinating ligand may be present in any effective amount. The catalyst coordinating ligand may preferably be present in an amount in the range of from about 1 mole % to about 50 mole % with respect to the amount of aryl halide, more preferably in the range of from about 2 mole % to about 25 mole % with respect to the amount of aryl halide, and even more preferably in an amount that is about 10 mole % with respect to the amount of aryl halide.

The solvent to be used in the iodination reaction may be any polar organic solvent, such as tetrahydrofuran, dioxane, xylene, n-alcohols, and mixtures thereof. In particular, alcohols such as n-butanol, n-pentanol, n-hexanol, n-heptanol may be used. Preferably, in embodiments, low-cost, high-boiling alcohols, such as n-propanol, n-butanol and n-pentanol, and combinations thereof are used as the solvent. In some embodiments, the iodination reaction solvent has a boiling point of at least about 100° C. In some further embodiments, the iodination reaction is carried out under pressure greater than standard pressure, in a solvent that has a boiling point of less than 100° C. at standard pressure.

The reaction is carried out by stirring under heating. The reaction is preferably carried out under heating to a temperature of 100° C. or more, more preferably 125° C. or more, and most preferably 130° C. or more. In addition, it may be desirable to reflux the solvent vapor, since iodine has sublimating properties and may deposit on the upper portion of the reaction vessel.

The time necessary for the reaction to run to completion may vary with the identities of the reactants and solvent system. For example, a reaction to form 4-iodobiphenyl, in which the catalyst is CuI and the catalyst coordinating ligand is 1,3-propanediamine, may be complete after approximately four (4) hours in a solvent of 1-hexanol, which has a boiling point of 156° C. However, the same reaction in a solvent of 1-pentanol, which has a boiling point of 136° C., may require a significantly longer reaction time—about 18 hours.

After the conclusion of the reaction, the reaction mixture obtained is allowed to cool to 80° C., and the reaction mixture obtained is separated. Reaction products may be separated by any known or later developed method. Liquid products, for example, may be separated by extraction and/or distillation, and solid products may be separated by crystallization. For example, in some embodiments, a reaction mixture may be diluted with 2 volume equivalents of 30% ammonium hydroxide solution and allowed to cool further, resulting in product crystallization. The reaction product of the iodination reaction may be purified by any known method, such as chromatography or recrystallization. For example, recrystallization of 4-iodobiphenyl from 1-hexane results in a highly pure product.

The separated reaction product may be purified by recrystallization. If the reaction product is purified by recrystallization, the reaction product is dissolved in an organic solvent, such as methylene chloride, toluene, ethyl acetate, higher alcohols or the like. The organic phase formed by the reaction product and solvent may be washed with a dilute aqueous solution of a sodium salt, such as sodium thiosulfate or sodium carbonate. The organic phase may be then washed with water, dried, and the solvent may be removed by distillation. The residue may be recrystallized from any suitable organic solvent. The organic solvent for recrystallization may be chosen from ethyl acetate, toluene, ethanol, and mixtures thereof. In addition, liquid products may be purified by vacuum distillation.

The iodination reaction described herein may produce high yields of highly pure aryl iodides. Aryl iodide yields of at least about 75%, particularly in the range of from about 85% to about 95%, and more particularly of about 90%, may be obtained. In addition, the aryl iodide recovered may be highly pure. The aryl iodides obtained may be at least 90% pure; in particular, the aryl iodides may be at least 95% pure; more particularly, the aryl iodides may be at least 98% pure. The purity of the aryl iodides may be confirmed by any known or later developed analytical techniques, including but not limited to high performance liquid chromatography, gas-liquid chromatography and nuclear magnetic resonance spectroscopy.

A tertiary amine may be prepared by Ullmann condensation of a secondary amine and the aryl iodide compound prepared by the above-described process. Specifically, triarylamines such as those used as hole transport small molecules and charge transport small molecules, may be prepared by Ullmann condensation of a diarylamine and an aryl iodide compound obtained by the process described above. A process by which triarylamines may be prepared is described in detail in, for example, U.S. Pat. No. 4,764,625 to Turner, et al., and as set forth below.

The diarylamine has the general formula $R_2R_3NH$ wherein $R_2$ and $R_3$ are the same or different members selected from the group consisting of substituted and unsubstituted aryl, alkaryl and aralkyl. Examples of these amines include but are not limited to diphenylamine, N,N'-3,4-(dimethyl)phenylamine, N,N'-bis(alkylphenyl)-(1,1'-biphenyl)-4,4'-diamine wherein the alkyl is, for example, methyl, ethyl, propyl, n-butyl, etc., N,N'-diphenyl-N,N'-bis(chlorophenyl)-(1,1'-biphenyl)-4,4'-diamine, N,N'-diphenyl-N,N'-bis(3-methylphenyl)-(1,1'-biphenyl)-4,4'-diamine, and N,N-diphenyl-N,N-bis(3-hydroxphenyl)-(1,1"-biphenyl)-4,4"-diamine.

The condensation reaction is conducted in the presence of potassium hydroxide and finely divided copper catalyst, in an inert atmosphere, such as argon, nitrogen, or methane. The condensation reaction may be conducted either in the absence of a solvent or with an inert saturated hydrocarbon solvent. The reaction mixture may be maintained at a temperature between about 120° C. and 190° C. for a period of time sufficient to substantially complete the reaction.

Any commercially available potassium hydroxide in flake or pellet form with a low water content can be employed. Examples of copper catalysts include but are not limited to, copper powder, cupric oxide, cuprous oxide, cuprous sulfate, cuprous sulfide, etc. In fact, any copper catalyst commonly used in the Ullmann condensation reaction may be used.

The ratio of base to amine should be such that the base is present as an excess in relation to the amine. This excess can range from about 1.5:1 to about 6:1 moles.

The temperature range for conducting the reaction can be from about 120° C. to about 190° C., with the preferred reaction temperature being from about 135° C. to about 165° C.

The Ullmann condensation reaction of the present invention may be carried out in the absence of a solvent when the intended product is very soluble at ambient temperature in inert, high-boiling hydrocarbon solvents. When the intended product is at least relatively insoluble at ambient temperature in an inert hydrocarbon solvent, the use of potassium hydroxide yields a relatively pure product which can be further highly purified by recrystallization from the same solvent.

The inert hydrocarbon solvent can be dodecane, tetradecane or any other hydrocarbon having an initial boiling point about above 170° C., or mixtures thereof. In particular, SOLTROL® 170 (initial b.p. 218° C.), which is a mixture of $C_{13}$–$C_{15}$ aliphatic hydrocarbons, and SOLTROL® 130 (initial b.p. 176° C.), available from Phillips Chemical Company, are suitable solvent systems. The SOLTROL® hydrocarbons dramatically reduce work-up times, yielding a much purer product while being less expensive solvents.

Triarylamines formed by the above-described processes may be used as charge transporting molecules in charge transporting layers. Specifically, photoconductive imaging members for photoconductive photoreceptors and electrophotographic imaging members may comprise at least a charge transport layer comprising at least one triarylamine formed by the above-described processes.

Thus, this invention provides a simple, economical method for producing aryl iodides using fairly inexpensive reagents and mild reaction conditions to produce excellent yields of highly pure product.

The following examples are provided for illustrative purposes only and are in no way intended to limit the scope of the invention.

EXAMPLES

Example 1

Preparation of Iodobenzene 15.7 g (0.1 mole) of bromobenzene is dissolved in 150 mL of n-pentanol. 2 equivalents of sodium iodide and 10 mole % of 1,3-propanediamine are added to the bromobenzene solution. The reaction mixture is refluxed at 130° C. for eighteen (18) hours to produce iodobenzene, as shown in reaction scheme (4).

[Insert Chemical Drawing (4)]

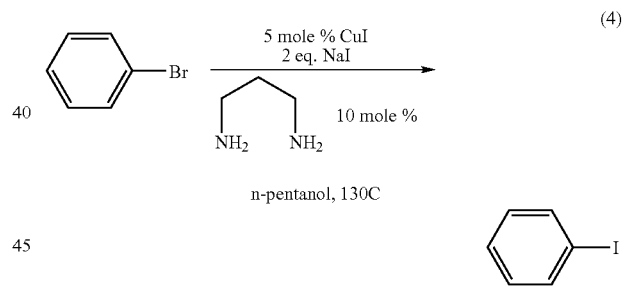

(4)

The reaction proceeds very rapidly. The reaction mixture is cooled to 80° C. and washed with a 30% ammonium hydroxide solution. The organic phase is washed with deionized water and brine. The organic phase is then dried over anhydrous sodium sulfate. The dried organic phase is subjected to rotary evaporation and/or vacuum distillation to afford a 92% yield of high purity iodobenzene.

Example 2

Preparation of 4-Iodobiphenyl 30 g of 4-bromobiphenyl is dissolved in 40 mL of n-pentanol. 2 equivalents of sodium iodide and 10 mole % of 1,3-propanediamine are added to the 4-bromobiphenyl solution. The reaction mixture is refluxed at 130° C. for sixteen (16) hours to produce 4-iodobiphenyl, as shown in reaction scheme (5).

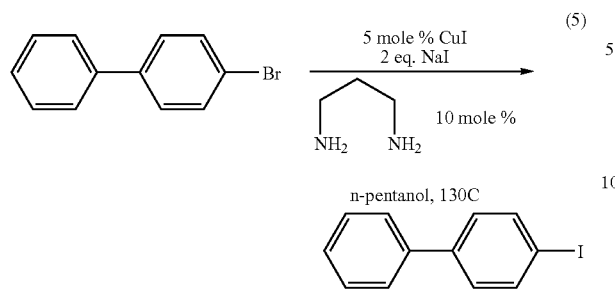

The reaction proceeds very rapidly. The reaction mixture is cooled to 80° C. and washed with a 30% ammonium hydroxide solution. The organic phase is washed with deionized water and brine. The organic phase is then dried over anhydrous sodium sulfate. The dried organic phase is subjected to rotary evaporation and/or vacuum distillation to afford crude product. The reaction mixture is recrystallized one time from n-pentanol, and a 92% yield of high purity 4-iodobiphenyl is obtained.

Example 3

Preparation of N,N-bis(phenyl)-4-biphenylamine 1143.5 g of recrystallized 4-iodobiphenyl, obtained in Example 2 is dissolved in 125 ml of ISOPAR M (trademark, Ashland Chemical), a commercially available mixture of high-boiling solvents having a boiling point of more than 200° C. 760 g of diphenylamine, 846 g of potassium carbonate, and 36.2 g of copper sulfate pentahydrate are added. The reaction mixture is placed under a nitrogen atmosphere and heated to 230° C. for two (2) hours. The reaction product is allowed to cool to 80° C. and 2000 ml of toluene is added. The reaction mixture is then slurry treated with 350 g of ENGELHARD F-20 activated clay (trademark, Engelhard Corporation). The clay is removed by filtration, and the solvent is removed by distillation under reduced pressure.

The residue is recrystallized in octane to provide 1127.8 g of N,N-bis(phenyl)-4-biphenylamine. The product is characterized as follows: yield: 86%, purity: 98.9, melting point: 117–118° C. The purity of the product is sufficient for use as a charge transport material.

While this invention has been described in conjunction with the exemplary embodiments outlined above, various alternatives, modifications, variations, improvements, and/or substantial equivalents, whether known or that are, or may be, presently unforeseen, may become apparent to those having at least ordinary skill in the art. Accordingly, the exemplary embodiments of the invention, as set forth above, are intended to be illustrative, not limiting. Various changes may be made without departing from the spirit and scope of the invention. Therefore, the systems, methods and devices according to this invention are intended to embrace all known or later-developed alternatives, modifications, variations, improvements, and/or substantial equivalents.

The invention claimed is:

1. A process for preparing an aryl iodide compound, comprising:
   reacting an aryl halide compound with a metal iodide, a metal catalyst and a catalyst coordinating ligand in at least one solvent to form an aryl iodide; and
   purifying the aryl iodide;
   wherein the solvent is heated to reflux during the reacting; wherein an aryl iodide yield of at least about 75% is obtained; and wherein the aryl iodide has a purity of at least 90%.

2. The process according to claim 1, wherein the aryl halide is selected from the group consisting of aryl bromides and aryl chlorides.

3. The process according to claim 1, wherein the aryl halide is selected from the group consisting of substituted and unsubstituted benzyl halides, cyclopentadienyl halides, biphenyl halides, terphenyl halides tolyl halides, naphthyl halides, anthryl halides, phenanthryl halides, pyryl halides, and fluorenyl halides.

4. The process according to claim 1, wherein the metal iodide is sodium iodide.

5. The process according to claim 1, wherein a molar ratio of the metal iodide to the aryl halide is in a range from about 1:1 to about 10:1.

6. The process according to claim 1, wherein a molar ratio of the metal iodide to the aryl halide is in a range from about 2:1 to about 5:1.

7. The process according to claim 1, wherein the metal catalyst is a copper catalyst.

8. The process according to claim 1, wherein the metal catalyst is present in an amount of from about 2 mole % to about 10 mole % with respect to an amount of aryl halide.

9. The process according to claim 1, wherein the metal catalyst is present in an amount of about 5 mole % with respect to an amount of aryl halide.

10. The process according to claim 1, wherein the catalyst coordinating ligand is a diamine ligand.

11. The process according to claim 1, wherein the catalyst coordinating ligand is 1,3-propanediamine.

12. The process according to claim 1, wherein the catalyst coordinating ligand is present in an amount of from about 1 mole % to about 50 mole % with respect to an amount of aryl halide.

13. The process according to claim 1, wherein the catalyst coordinating ligand is present in an amount of from about 2 mole % to about 25 mole % with respect to an amount of aryl halide.

14. The process according to claim 1, wherein the at least one solvent is selected from the group consisting of tetrahydrafuran, dioxane, xylene, alcohols, and mixtures thereof.

15. The process according to claim 1, wherein the at least one solvent is selected from the group consisting of n-butanol, n-pentanol, n-hexanol, n-heptanol and mixtures thereof.

16. The process according to claim 1, wherein the solvent is heated to reflux at a temperature of at least about 100° C.

17. The process according to claim 1, wherein the purifying is performed by recrystallization.

* * * * *